(12) United States Patent
Hamamah et al.

(10) Patent No.: US 9,090,938 B2
(45) Date of Patent: Jul. 28, 2015

(54) METHODS FOR SELECTING COMPETENT OOCYTES AND COMPETENT EMBRYOS WITH HIGH POTENTIAL FOR PREGNANCY OUTCOME

(71) Applicants: Samir Hamamah, Montpellier (FR); Said Assou, Montpellier (FR); John De Vos, Montpellier (FR)

(72) Inventors: Samir Hamamah, Montpellier (FR); Said Assou, Montpellier (FR); John De Vos, Montpellier (FR)

(73) Assignees: Institut National de la Sante et de la Recherche Medicale (INSERM), Paris (FR); Universite de Montpellier 1, Montpellier Cedex (FR); Centre Hospaitalier Univeritaire de Montpelier, Montpellier (FR)

( * ) Notice: Subject to any disclaimer, the term of this patent is extended or adjusted under 35 U.S.C. 154(b) by 0 days.

(21) Appl. No.: 14/627,394

(22) Filed: Feb. 20, 2015

(65) Prior Publication Data

US 2015/0167079 A1    Jun. 18, 2015

Related U.S. Application Data

(63) Continuation of application No. 13/823,763, filed as application No. PCT/EP2011/068184 on Oct. 18, 2011.

(30) Foreign Application Priority Data

Oct. 18, 2010    (EP) ..................................... 10306132

(51) Int. Cl.
C12Q 1/66    (2006.01)
C12Q 1/68    (2006.01)
A61B 17/43    (2006.01)
G01N 33/68    (2006.01)

(52) U.S. Cl.
CPC .............. *C12Q 1/6881* (2013.01); *A61B 17/43* (2013.01); *C12Q 1/66* (2013.01); *C12Q 2600/158* (2013.01); *C12Q 2600/16* (2013.01); *G01N 33/689* (2013.01)

(58) Field of Classification Search
None
See application file for complete search history.

(56) References Cited

FOREIGN PATENT DOCUMENTS

WO    2010/118991 A1    10/2010

OTHER PUBLICATIONS

Assou et al., "A non-invasive test for assessing embryo potential by gene expression profiles of human cumulus cells: a proof of concept study", Molecular Human Reproduction, Dec. 1, 2008, pp. 711-719, vol. 14, No. 12, Oxford University Press, GB.
Anderson et al., "Cumulus gene expression as a predictor of human oocyte fertilisation, embryo development and competence to establish a pregnancy", Reproduction, Oct. 2009, pp. 629-637, vol. 138, No. 4.
Assou et al., "Human cumulus cells as biomarkers for embryo and pregnancy outcomes", Molecular Human Reproduction, Aug. 1, 2010, pp. 531-538, vol. 16, No. 8, Oxford University Press, GB.
Van Montfoort et al., "Differential gene expression in cumulus cells as a prognostic indicator of embryo viability: a microarray analysis", Molecular Human Reproduction, Mar. 2008, pp. 157-168, vol. 14, No. 3.
Huang; Wells, "The human oocyte and cumulus cells relationship: new insights from the cumulus cell trascriptome", Molecular Human Reproduction, Oct. 1, 2010, pp. 715-725, vol. 16, No. 10, Oxford University Press, GB.
Assou et al., "The human cumulus-oocyte complex gene-expression profile", Human Reproduction, 2006, pp. 1705-1719, vol. 21, No. 7.

*Primary Examiner* — Christopher M Babic
*Assistant Examiner* — Sahana Kaup
(74) *Attorney, Agent, or Firm* — Whitham Curtis Christofferson & Cook, PC

(57) ABSTRACT

The present invention relates to a method for selecting a competent oocyte or a competent embryo.

6 Claims, 1 Drawing Sheet

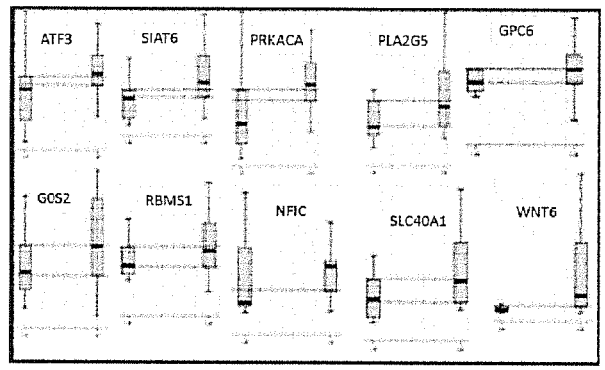

METHODS FOR SELECTING COMPETENT OOCYTES AND COMPETENT EMBRYOS WITH HIGH POTENTIAL FOR PREGNANCY OUTCOME

CROSS-REFERENCE TO RELATED APPLICATIONS

This application is a continuation application of U.S. Ser. No. 13/823,763 filed May 9, 2013, which was a Rule 371 application of PCT/EP2011/068184 filed Oct. 18, 2011.

FIELD OF THE INVENTION

The present invention relates to a method for selecting a competent oocyte or a competent embryo.

BACKGROUND OF THE INVENTION

In assisted reproductive technology (ART), pregnancy and birth rates following in vitro fertilization (IVF) attempts remain low. Indeed, 2 out of 3 IVF cycles fail to result in pregnancy (SART 2004) and more than 8 out of 10 transferred embryos fail to implant (Kovalevsky and Patrizio, 2005). In addition, more than 50% of IVF-born babies are from multiple gestations (Reddy et al., 2007). Preterm deliveries that result from multiple pregnancies caused by ART are estimated to account for approximately $890 million of U.S. health care costs annually (Bromer and Seli, 2008).

Subjective morphological parameters are still a primary criterion to select healthy embryos used for in IVF and ICSI programs. However, such criteria do not truly predict the competence of an embryo. Many studies have shown that a combination of several different morphologic criteria leads to more accurate embryo selection (Balaban and Urman, 2006; La Sala et al., 2008; Scott et al., 2000). Morphological criteria for embryo selection are assessed on the day of transfer, and are principally based on early embryonic cleavage (25-27 h post insemination), the number and size of blastomeres on day two or day three, fragmentation percentage and the presence of multi-nucleation in the 4 or 8 cell stage (Fenwick et al., 2002).

However, a recent study has shown that the selection of oocytes for insemination does not improve outcome of ART as compared to the transfer of all available embryos, irrespective of their quality (La Sala et al., 2008). There is a need to identify viable embryos with the highest implantation potential to increase IVF success rates, reduce the number of embryos for fresh replacement and lower multiple pregnancy rates.

For all these reasons, several biomarkers for embryo selection are currently being investigated (Haouzi et al., 2008; Pearson, 2006). As embryos that result in pregnancy differ in their metabolic profiles compared to embryos that do not, some studies are trying to identify a molecular signature that can be detected by non-invasive evaluation of the embryo culture medium (Brison et al., 2004; Gardner et al., 2001; Sakkas and Gardner, 2005; Seli et al., 2007; Zhu et al., 2007).

Genomics are also providing vital knowledge of genetic and cellular function during embryonic development. (McKenzie et al., 2004) and (Feuerstein et al., 2007) have reported, that the expression of several genes in cumulus cells, such as cyclooxygenase 2 (COX2), was indicative of oocyte and embryo quality. Gremlin 1 (GREM1), hyaluronic acid synthase 2 (HAS2), steroidogenic acute regulatory protein (STAR), stearoyl-coenzyme A desaturase 1 and 5 (SCD1 and 5), amphiregulin (AREG) and pentraxin 3 (PTX3) have also been shown to be positively correlated with embryo quality (Zhang et al., 2005). More recently, the expression of glutathione peroxidase 3 (GPX3), chemokine receptor 4 (CXCR4), cyclin D2 (CCND2) and catenin delta 1 (CTNND1) in human cumulus cells have been shown to be inversely correlated with embryo quality, based on early-cleavage rates during embryonic development (van Montfoort et al., 2008). But, despite the fact that early cleavage has been shown to be a reliable biomarker for predicting pregnancy (Lundin et al., 2001; Van Montfoort et al., 2004; Yang et al., 2007), these gene expression profiles of cumulus cells have not been studied with respect to pregnancy outcome.

(Assou et al., 2008) and (Fourar et al., 2008) have reported that BCL2-like 11 (BCL2L11), CASP8 and FADD-like apoptosis regulator (CFLAR), matrix metallopeptidase 14 (MMP14), nuclear factor UB (NFIB) and phosphoenolpyruvate carboxykinase 1 (PCK1) gene expression profiles were associated with a successful pregnancy.

These genes expression profiles are associated with pregnancy outcome in general but specific oocyte or embryo qualities as capacity of an embryo to implant or to develop without arrest have not been studied.

SUMMARY OF THE INVENTION

The present invention relates to a method for selecting an oocyte that will produce, upon fertilization, a viable embryo with a high implantation rate leading to pregnancy, comprising the step of measuring the expression level of 10 genes in a cumulus cell surrounding said oocyte;

wherein said genes are ATF3, SIAT6, PRKACA, PLA2G5, GPC6, G0S2, RBMS1, NFIC, SLC40A1 and WNT6 and wherein the oocyte is selected if said cumulus cell does not overexpress any of said 10 genes.

The present invention also relates to a method for selecting an embryo with a high implantation rate leading to pregnancy, comprising the step of measuring the expression level of 10 genes in a cumulus cell surrounding the embryo, wherein said genes are ATF3, SIAT6, PRKACA, PLA2G5, GPC6, G0S2, RBMS1, NFIC, SLC40A1 and WNT6 and wherein the embryo is selected if said cumulus cell does not overexpress any of said 10 genes.

DETAILED DESCRIPTION OF THE INVENTION

The inventors have determined as set of 10 genes expressed in cumulus cells that are biomarkers for embryo potential and pregnancy outcome. They demonstrated that genes expression profile of cumulus cells which surrounds oocyte correlated to different pregnancy outcomes, allowing the identification of a specific expression signature of embryos developing toward pregnancy. Their results indicate that analysis of cumulus cells surrounding the oocyte is a non-invasive approach for embryo selection.

Set of Predictive Genes

All the genes pertaining to the invention are known per se, and are listed in the below Table A. Table A present the set of genes whose combined expression profile has been shown to be informative for selecting an oocyte that will produce, upon fertilization, a viable embryo with a high implantation rate leading to pregnancy or for selecting a competent embryo with a high implantation potential leading to pregnancy.

TABLE A set of predictive genes.

| Gene symbol | Gene name | Gene ID |
|---|---|---|
| ATF3 | activating transcription factor 3 | 467 |
| SIAT6 | ST3 beta-galactoside alpha-2,3-sialyltransferase 3 | 6487 |
| PRKACA | protein kinase, cAMP-dependent, catalytic, alpha | 5566 |
| PLA2G5 | phospholipase A2, group V | 5322 |
| GPC6 | glypican 6 | 10082 |
| G0S2 | G0/G1 switch 2 | 50486 |
| RBMS1 | RNA binding motif, single stranded interacting protein 1 | 5937 |
| NFIC | nuclear factor I/C (CCAAT-binding transcription factor) | 4782 |
| SLC40A1 | solute carrier family 40 (iron-regulated transporter), member 1 | 30061 |
| WNT6 | wingless-type MMTV integration site family, member 6 | 7475 |

An object of the invention relates to a method for selecting an oocyte that will produce, upon fertilization, a viable embryo with a high implantation rate leading to pregnancy, comprising the step of measuring the expression level of 10 genes in a cumulus cell surrounding said oocyte; wherein said genes are ATF3, SIAT6, PRKACA, PLA2G5, GPC6, G0S2, RBMS1, NFIC, SLC40A1 and WNT6 and wherein the oocyte is selected if said cumulus cell does not overexpress any of said 10 genes.

The methods of the invention may further comprise a step consisting of comparing the expression level of the genes in the sample with a control, wherein detecting differential in the expression level of the genes between the sample and the control is indicative whether the oocyte produces, upon fertilization, a viable embryo with a high implantation rate leading to pregnancy or the embryo is with a high implantation rate leading to pregnancy.

The control may consist in sample comprising cumulus cells associated with a competent oocyte or in a sample comprising cumulus cells associated with an unfertilized oocyte or a non competent oocyte.

Preferably, the control consists in sample comprising cumulus cells associated with a competent oocyte.

A used herein the term "competent oocyte" refers to a female gamete or egg that when fertilized produces a viable embryo with a high implantation rate leading to pregnancy.

According to the invention, the oocyte may result from a natural cycle, a modified natural cycle or a stimulated cycle for cIVF or ICSI. The term "natural cycle" refers to the natural cycle by which the female or woman produces an oocyte. The term "modified natural cycle" refers to the process by which, the female or woman produces an oocyte or two under a mild ovarian stimulation with GnRH antagonists associated with recombinant FSH or hMG. The term "stimulated cycle" refers to the process by which a female or a woman produces one or more oocytes under stimulation with GnRH agonists or antagonists associated with recombinant FSH or hMG.

The term "cumulus cell" refers to a cell comprised in a mass of cells that surrounds an oocyte. These cells are believed to be involved in providing an oocyte some of its nutritional, energy and or other requirements that are necessary to yield a viable embryo upon fertilization.

The expression "a cumulus cell overexpressed a gene" means that the level of expression of said gene in the cumulus cell is higher than the expression level of said gene in a control sample.

Typically, the level of expression of genes may be measured by various techniques such as DNA microarray, quantitative RT-PCR, semi-quantitative RT-PCR or by proteomic approaches (ELISA method, Western blots . . . ).

Typically, an overexpressed gene has a level of expression at least 1.5, at least 2, at least 2.5, at least 5, at least 7.5 or at least 10 times higher than the level of expression of said gene in a control sample.

Preferably, the level of expression is measured by quantitative RT-PCR and an overexpressed gene has a level of expression at least 1.5, at least 2, or at least 2.5 times higher than the level of expression of said gene in a control sample.

The control sample may be a cumulus cell associated with a competent oocyte or embryo.

The methods of the invention are applicable preferably to women but may be applicable to other mammals (e.g., primates, dogs, cats, pigs, cows . . . ).

The methods of the invention are particularly suitable for assessing the efficacy of an in vitro fertilization treatment. Accordingly the invention also relates to a method for assessing the efficacy of a controlled ovarian hyperstimulation (COS) protocol in a female subject comprising:

i) providing from said female subject at least one oocyte with its cumulus cells;

ii) determining by a method of the invention whether said oocyte is an oocyte that will produce, upon fertilization, a viable embryo with a high implantation rate leading to pregnancy.

Then after such a method, the embryologist may select the oocytes that will produce, upon fertilization, a viable embryo with a high implantation rate leading to pregnancies and in vitro fertilized them through a classical in vitro fertilization (cIVF) protocol or under an intracytoplasmic sperm injection (ICSI) protocol.

A further object of the invention relates to a method for monitoring the efficacy of a controlled ovarian hyperstimulation (COS) protocol comprising:

i) isolating from said woman at least one oocyte with its cumulus cells under natural, modified or stimulated cycles;

ii) determining by a method of the invention whether said oocyte is an oocyte that will produce, upon fertilization, a viable embryo with a high implantation rate leading to pregnancy;

iii) and monitoring the efficacy of COS treatment based on whether it results in an oocyte that will produce, upon fertilization, a viable embryo with a high implantation rate leading to pregnancy.

The COS treatment may be based on at least one active ingredient selected from the group consisting of GnRH agonists or antagonists associated with recombinant FSH or hMG.

The present invention also relates to a method for selecting an embryo with a high implantation rate leading to pregnancy, comprising a step of measuring the expression level of 10 genes in a cumulus cell surrounding the embryo, wherein said genes are ATF3, SIAT6, PRKACA, PLA2G5, GPC6, G0S2, RBMS1, NFIC, SLC40A1 and WNT6 and wherein the embryo is selected if said cumulus cell does not overexpress any of said 10 genes.

The term "embryo" refers to a fertilized oocyte or zygote. Said fertilization may intervene under a classical in vitro fertilization (cIVF) or under an intracytoplasmic sperm injection (ICSI) protocol.

The term "classical in vitro fertilization" or "cIVF" refers to a process by which oocytes are fertilized by sperm outside of the body, in vitro. IVF is a major treatment in infertility when in vivo conception has failed. The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization, especially that associated with sperm donation.

The term "competent embryo" refers to an embryo with a high implantation rate leading to pregnancy. The term "high implantation rate" means the potential of the embryo when transferred in uterus, to be implanted in the uterine environment and to give rise to a viable fetus, which in turn develops into a viable offspring absent a procedure or event that terminates said pregnancy.

The methods of the invention may further comprise a step consisting of comparing the expression level of the genes in the sample with a control, wherein detecting differential in the expression level of the genes between the sample and the control is indicative whether the embryo is competent.

The control may consist in sample comprising cumulus cells associated with an embryo that gives rise to a viable fetus or in a sample comprising cumulus cells associated with an embryo that does not give rise to a viable fetus.

Preferably, the control consists in sample comprising cumulus cells associated with an embryo that gives rise to a viable fetus.

It is to note that the methods of the invention leads to an independence from morphological considerations of the embryo. Two embryos may have the same morphological aspects but by a method of the invention may present a different implantation rate leading to pregnancy.

The methods of the invention are applicable preferably to women but may be applicable to other mammals (e.g. primates, dogs, cats, pigs, cows . . . ).

The present invention also relates to a method for determining whether an embryo is an embryo with a high implantation rate leading to pregnancy, comprising a step consisting in measuring the expression level of 10 genes in a cumulus cell surrounding the embryo, wherein said genes are ATF3, SIAT6, PRKACA, PLA2G5, GPC6, G0S2, RBMS1, NFIC, SLC40A1 and WNT6.

The present invention also relates to a method for determining whether an embryo is an embryo with a high implantation rate leading to pregnancy, comprising:
 i) providing an oocyte with its cumulus cells
 ii) in vitro fertilizing said oocyte
 iii) determining whether the embryo that results from step ii) is competent by determining by a method of the invention whether said oocyte of step i), is an oocyte that will produce, upon fertilization, a viable embryo with a high implantation rate leading to pregnancy.

The methods of the invention are particularly suitable for enhancing the pregnancy outcome of a female. Accordingly the invention also relates to a method for enhancing the pregnancy outcome of a female comprising:
 i) selecting an embryo with a high implantation rate leading to pregnancy by performing a method of the invention
 iii) implanting the embryo selected at step i) in the uterus of said female.

The method as above described will thus help embryologist to avoid the transfer in uterus of embryos with a poor potential for pregnancy out come.

The method as above described is also particularly suitable for avoiding multiple pregnancies by selecting the competent embryo able to lead to an implantation and a pregnancy.

In all above cases, the methods described the relationship between genes expression profile of cumulus cells and embryo and pregnancy outcomes.

Methods for Determining the Expression Level of the Genes of the Invention:

Determination of the expression level of the genes as above described in Table A can be performed by a variety of techniques. Generally, the expression level as determined is a relative expression level.

More preferably, the determination comprises contacting the sample with selective reagents such as probes, primers or ligands, and thereby detecting the presence, or measuring the amount, of polypeptide or nucleic acids of interest originally in the sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a preferred embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from cumulus cells and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

In this context, the invention further provides a DNA chip comprising a solid support which carries nucleic acids that are specific to the genes listed in table A.

Other methods for determining the expression level of said genes include the determination of the quantity of proteins encoded by said genes.

Such methods comprise contacting the sample with a binding partner capable of selectively interacting with a marker protein present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate (s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be preferred. IHC specifically provides a method of detecting targets in a sample or tissue specimen in situ. The overall cellular integrity of the sample is maintained in IHC, thus allowing detection of both the presence and location of the targets of interest. Typically a sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section (e.g. a sample comprising cumulus cells) may be mounted on a slide or other support after incubation with antibodies directed against the proteins encoded by the genes of interest. Then, microscopic inspections in the sample mounted on a suitable solid support may be performed. For the production of photomicrographs, sections comprising samples may be mounted on a glass slide or other planar support, to highlight by selective staining the presence of the proteins of interest.

Therefore IHC samples may include, for instance: (a) preparations comprising cumulus cells (b) fixed and embedded said cells and (c) detecting the proteins of interest in said cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

The invention also relates to a kit for performing the methods as above described, wherein said kit comprises means for measuring the expression level the levels of the genes of Table A that are indicative whether the oocyte or the embryo is competent.

The invention will be further illustrated by the following figures and examples. However, these examples and figures should not be interpreted in any way as limiting the scope of the present invention.

FIGURE

FIG. 1: Box plot of set of predictive genes.

For each gene, the relative intensities of embryo's cumulus cells that gave pregnancy are shown at the left side and the relative intensities of those that did not give pregnancy at the right side.

EXAMPLE

A Non-Invasive Test for Assessing Embryo Potential by Gene Expression Profiles of Human Cumulus Cells Material & Methods:

Patients and IVF Treatment:

In this retrospective study, normo-responder patients (n=30) aged of 30.9 years±2.5 and referred to our centre for ICSI (Intra Cytoplasmic Sperm Injection) for male infertility factor were studied. Patients were stimulated with a combination of GnRH agonist or antagonist with recombinant FSH (GonalF, Puregon; respectively of Merck-Serono and Organon) or with hMG (Menopur, Ferring). Ovarian response was evaluated by serum estradiol level and ultrasound examination to monitor follicle development. Retrieval of oocytes was performed 36 hours after hCG administration (5000 IU), under ultrasound guidance.

Assessment of Embryo Quality:

On day 2 and 3 postmicroinjection, the quality parameters of individually cultured embryo were evaluated using the number of blastomeres and the degree of fragmentation as criteria (grade 1-2: equally sized blastomeres and 0-20% fragmentation, grade 3-4: no equally sized blastomeres and more than 20% fragmentation. A top-quality embryo was defined on day 3 as 6-8 cells, equally sized blastomeres and no fragmentation. One or two embryos were transferred on day 3 after oocyte retrieval. Clinical pregnancy was evaluated two and six weeks after embryo transfer based respectively on serum Beta-hCG and ultrasound examination (presence of gestational sac with heart beat).

Cumulus Cells:

All cumulus cells (CC) samples were frozen on egg collection day. Then, one to 3 CC samples per patient were randomly selected for microarray analysis. A total of 50 CC samples were collected from 50 single oocytes and analyzed individually: 34 CC from grade 1-2 embryos (n=20 patients), 11 CC from grade 3-4 embryos (n=10 patients) and 5 CC from unfertilized oocytes (n=5 patients) (Table 1).

TABLE 1

The Characteristics of cumulus cells samples in this study

| | 30 patients 45 CC | | | 5 Patients 5 CC |
|---|---|---|---|---|
| | G1/2 (34 CC) | | G3/4 (11 CC) | cumulus cells from |
| | P+ | P− | NT | unfertilized oocyte (5 CC) |
| chips nbr | 18 | 16 | 11 | 5 |
| Patients nbr | 11 | 9 | 10 | 5 |
| CC nbr | 18 | 16 | 11 | 5 |

CC: cumulus cells, P+: cumulus cells from embryos with positive pregnancy outcome, P−: cumulus cells from embryos without pregnancy outcome, G1/2 cumulus cells from grade 1-2 embryos, G3/4: cumulus cells from grade 3-4 embryos, NT: no transfer.

The data analysis was performed under double blind conditions in which pregnancy outcome was disclosed only after microarrays were hybridized. Regarding pregnancy outcome, the 45 CC from fertilized oocytes included 16 CC from grade 1-2 embryos that did not result into pregnancy (n=9 patients), 18 CC associated with a positive pregnancy outcome (n=11 patients) and 11 CC from grade 3-4 embryos that were not transferred. Cumulus cells were stripped immediately following oocyte recovery (<40 h post hCG administration). Cumulus cells were mechanically removed and washed in culture medium and immediately frozen at −80° C. in RLT RNA extraction buffer (RNeasy kit, Qiagen, Valencia, Calif., USA) before RNA extraction.

Granulosa Cells:

An independent group of normo responder patients (n=8) (age 34.8 years±3.2) referred for ICSI program for male infertility factor was selected for granulosa cells collection (8 samples). Immediately after oocyte recovery, follicular fluids from matures follicles (>17 mm) of the same patient were pooled, after removal of the cumulus oocyte complex and diluted in ⅓ volume of HBSS solution (BioWhittaker) in 50 ml batches, representing one sample. Granulosa cells purification was adapted from the protocol by (Kolena et al., 1983). Following a 20 min. centrifugation at 500 g in swinging buckets, granulosa cells were collected on a Ficoll cushion (12 ml Lymphocyte separation medium, BioWhittaker). They were successively washed in HBSS and PBS, incubated 5 min. in blood lysis buffer ($KHCO_3$ 10 mM, NH4Cl 150 mM, EDTA 0.1 mM) to remove red blood cells, counted and pelleted in PBS before lysis in RLT buffer (Quiagen) and storage at −80° C. The number of follicular puncture and the number of purified granulosa cells ranged from 6 to 12 and from $2\,10^6$ to $9\,10^6$ respectively.

Complementary RNA (cRNA) Preparation and Microarray Hybridization:

CC and granulosa cells RNA was extracted using the micro RNeasy Kit (Qiagen). The total RNA quantity was measured with a Nanodrop ND-1000 spectrophotometer (Nanodrop Technologies Inc., DE, USA) and RNA integrity was assessed with an Agilent 2100 Bioanalyzer (Agilent, Palo Alto, Calif., USA). cRNA was prepared with two rounds of amplification according to the manufacturer's protocol "double amplification" (Two-Cycle cDNA Synthesis Kit, Invitrogen) starting from total RNA (ranging from 70 ng to 100 ng). cRNA obtained after the first amplification ranged from 0.1 µg/µl to 1.9 µg/µl and after the second amplification ranged from 1.6 µg/µl to 4.5 µg/µl.

Labelled fragmented cRNA (12 µg) was hybridized to oligonucleotide probes on an Affymetrix HG-U133 Plus 2.0 array containing 54,675 sets of oligonucleotide probes ("probeset") which correspond to ≈30,000 unique human genes or predicted genes. Each cumulus and granulosa sample was put individually on a microarray chip.

Data Processing:

Scanned GeneChip images were processed using Affymetrix GCOS1.4 software to obtain an intensity value and a detection call (present, marginal or absent) for each probeset, using the default analysis settings and global scaling as first normalization method, with a trimmed mean target intensity value (TGT) of each array arbitrarily set to 100. Probe intensities were derived using the MAS5.0 algorithm. This algorithm also determines whether a gene is expressed with a defined confidence level or not ("detection call"). This "call" can either be "present" (when the perfect match probes are significantly more hybridized than the mismatch probes, p-value <0.04), "marginal" (for p-values >0.04 and <0.06) or "absent" (p-value >0.06). The microarray data were obtained in our laboratory in agreement with the Minimal Information about a Microarray Experiment MIAME recommendations (Brazma et al. 2001).

Data Analysis and Visualisation:

Significant Analysis of microarrays (SAM) (Tusher et al., 2001) (http://www-stat.stanford.edu/~tibs/SAM/) was used to identify genes whose expression varied significantly between sample groups. SAM provides mean or median fold change values (FC) and a false discovery rate (FDR) confidence percentage based on data permutation (mean fold change >2 and FDR <5%). Array analysis allowing the comparison of gene expression profile between cumulus cell samples and granulosa cell samples is first based on the significant RNA detection (detection call "present" or "absent") and then, submitted to a SAM (Significant Analysis of microarrays) to identify genes whose expression varied significantly between sample groups. To perform the comparison of gene expression profile between cumulus cell samples according embryonic quality and/or pregnancy outcome, a non-supervised selection of probesets using a variation coefficient (CV ≥40%) and a Absent/Present "detection call" filter was performed before the SAM. To compare profile expression of cumulus cells from altered (grade 3-4) and good (grade 1-2) embryonic development, or from embryos leading, or not, to a pregnancy, we performed an unsupervised classification with both principal component analysis (PCA) and hierarchical clustering (de Hoon et al., 2004; Eisen et al., 1998). The PCA involved original scripts based on the R statistics software through the RAGE web interface (http://rage.montp.inserm.fr) (Reme et al., 2008). Hierarchical clustering analysis based on the expression levels of varying probes were performed with the CLUSTER and TREEVIEW software packages. To uncover functional biological networks and top canonical pathways, we imported gene expression signatures into the Ingenuity Pathways Analysis (IPA) Software (Ingenuity Systems, Redwood City, Calif., USA).

Quantitative RT-PCR Analyses:

For qRT-PCR analysis, 10 CC samples used in the microarray experiments were selected according to their pregnancy outcome (5 CC samples associated to a negative outcome and 5 to a positive outcome corresponding to 10 patients). Labelled cRNA (1 µg) from the patient was used to generate first strand cDNA. These cDNAs (5 µl of a 1/10 dilution) were used for real-time quantitative PCR reactions according to the manufacturer's recommendations (Applied Biosystems). The 20 µl reaction mixture consisted of cDNA (5 µl), 1 µM of primers and 10 µl of Taqman Universal PCR Master Mix (Applied Biosystem). The amplification was measured during 40 cycles with an annealing temperature at 60° C. The amount of PCR product produced in every cycle step of the PCR reaction is monitored by TaqMan probe. A threshold is set in the exponential phase of the amplification curve, from which the cycle number ("Ct" for "Cycle Threshold") is read off. The Ct-value is used in the calculation of relative mRNA transcript levels. Effectiveness (E) of the PCR was measured. This effectiveness is obtained by a standard curve corresponding to the primers used. Quantitative reverse transcriptase polymerase chain reaction (QRT-PCR) was performed using the ABI Prism 7000 sequence detection system (Applied Biosystems) and normalized to PGK1 for each sample using the following formula: $E_{tested\ primer}^{\Delta Ct}/E_{PGK1}^{\Delta Ct}(E=10^{-1/slope})$, $\Delta Ct=Ct$ control–Ct unknown, control=one CC sample of the non-pregnant group). Each sample was analysed in duplicate, and multiple water blanks were included with the analysis.

Results

Gene Expression Profile of CC According to Embryo Outcome:

To identify a gene expression profile in CC that correlated with embryo outcome, we established a gene expression signature for each outcome category: CC of unfertilized oocytes, CC from oocytes that resulted in embryo development but extensive fragmentation (grade 3-4), and CC from oocytes that resulted in embryo development with no or limited fragmentation (grade 1-2). Granulosa cells samples were taken as a reference tissue (control). Indeed, granulosa cells are cells closely related to CC as opposed to other adult tissues. The use of this reference tissue lowered the number of differentially expressed genes related to crude lineage differences, thus facilitating the identification of subtle variation in the CC/oocyte interplay. A SAM analysis showed that 2605 genes were upregulated in the unfertilized group, 2739 in the grade 3/4 group and 2482 in the grade 1-2 group with a FDR <5%. Conversely, 4270, 4349 and 4483 genes, were downregulated, respectively. These lists of genes were then intersected to determine their overlap. While 449 up and 890 down expressed genes were in common in all three groups, each category displayed a specific gene expression profile. Interestingly, 860 up-regulated genes, including for example Galanin and Gap Junction A5 (GJA5), and 1416 down-regulated genes, including HLA-G and EGR1 were specifically modulated in cumulus cells associated to a good morphological embryonic quality. It must be noted that although the grade 1-2 group displayed a strong gene expression profile, this group was heterogeneous regarding to pregnancy outcome and included 18 CC samples associated with embryos that resulted in pregnancy (including 4 twin pregnancies) but also 16 CC samples associated with embryos that failed to give rise to pregnancy.

Gene Expression Profile of CC According to Pregnancy Outcome:

CC samples were therefore compared according to the pregnancy outcome. A SAM analysis delineated a "pregnancy outcome" list of 630 genes that varied significantly (FDR <5%) between the two group of patients (pregnancy versus no pregnancy). PCA and hierarchical clustering confirmed that this 630 gene list indeed segregated a majority of CC samples associated with pregnancy from those associated with no pregnancy. Of note, genes from the "pregnancy outcome" list were predominantly upregulated in samples associated with a good outcome. The "pregnancy outcome" expression signature was particularly marked in a sub-group of 10 CC samples from embryos associated to the "pregnancy" group.

Functional Annotation of the Pregnancy Outcome Gene List:

To investigate biological processes correlated to embryo achieving pregnancy, Ingenuity and Pubmed databases were used to annotate the 630 genes from the "pregnancy outcome" gene list. Among genes whose overexpression is associated with pregnancy, the most significantly overrepresented pathways were "oxidative stress", "TR/RXR activation", "G2/M transition of the cell cycle", "xenobiotic metabolism" and "NFKappaB" signalling. Among these pathways, the most representative genes were interleukins, chemokines, adaptor proteins and kinases: IL1Beta (×4.5 in pregnancy samples versus no pregnancy, P=0.001), IL16 (×4.8, P=0.001), IL8 (×2.6, P=0.007), IL1RN (×2.1, P=0.0051), IL17RC (×3.6, P=0.001), TIRAP (×8.0, P=0.001), CXCL12 (×3.1, P=0.001), CCR5 (×2.6, P=0.0051), and PCK1 (×3.4, P=0.001). Strikingly, numerous genes involved in the regulation of apoptosis were significantly modulated in CC samples from oocytes resulting in a pregnancy. These genes were BCL2L11 (×6,9, P<0.001), CRADD (×2, P=0.0036), NEMO (×4.6, P<0.001), BCL10 (×3.1, P=<0.001), SERPINB8 (×9.1, P<0.001). and TNFSF13 (×2.5, P=0.0038).

On the other hand, genes associated with no pregnancy were correlated with the following pathways: G2/M DNA damage and checkpoint regulation of the cell cycle, "Sonic hedgehog", "IGF-1", "complement system" and "Wnt/Beta-catenin" signalling. Representative genes correlated with no pregnancy included NFIB (×0.3, P<0.001), MAD2L1 (×0.4, P<0.001) and IGF1R (×0.4, P<0.001).

SAM Analysis:

The SAM analysis of CC according to pregnancy outcome identified the 45 genes of Table B that are biomarkers for embryo potential that would differentiate between oocytes that produced embryos resulting in a pregnancy versus those that did not result in pregnancy based on genes expression of CC analysis. QRT-PCR was used to confirm independently the microarray data. We analyzed the differential expression of 36 up-regulated genes and 9 down-regulated genes between CC from grade 1-2 embryos did not achieve pregnancy and CC from grade 1-2 embryos achieving pregnancy.

TABLE B set of predictive genes.

| Gene Symbol | Gene name | Gene ID |
|---|---|---|
| WNT6 | wingless-type MMTV integration site family, member 6 | 7475 |
| LRCH4 | leucine-rich repeats and calponin homology (CH) domain containing | 4034 |
| PAX8 | paired box 8 | 7849 |
| CABP4 | calcium binding protein 4 | 57010 |
| PDE5A | phosphodiesterase 5A, cGMP-specific | 8654 |
| BCL2L11 | BCL2-like 11 (apoptosis facilitator) | 10018 |
| PCK1 | phosphoenolpyruvate carboxykinase 1 (soluble) | 5105 |
| TCF20 | transcription factor 20 (AR1) | 6942 |
| SLAMF6 | SLAM family member 6 | 114836 |
| EPOR | erythropoietin receptor | 2057 |
| CACNG6 | calcium channel, voltage-dependent, gamma subunit 6 | 59285 |
| NLRP1 | NLR family, pyrin domain containing 1 | 22861 |
| PECAM1 | platelet/endothelial cell adhesion molecule | 5175 |
| NOS1 | nitric oxide synthase 1 (neuronal) | 4842 |
| ATF3 | Activating transcription factor 3 | 467 |
| KRTAP8 | keratin associated protein 8-1 | 337879 |
| GRIK5 | Glutamate receptor, ionotropic, kainate 5 | 2901 |
| SLC24A3 | solute carrier family 24 (sodium/potassium/calcium exchanger), member 3 | 57419 |
| SLC5A12 | solute carrier family 5 (sodium/glucose cotransporter), member 12 | 159963 |
| SLCA10A2 | Solute carrier family 10 (sodium/bile acid cotransporter family), member 2 | 6555 |
| SLCO1A2 | solute carrier organic anion transporter family, member 1A2 | 6579 |
| SLC25A5 | solute carrier family 25 (mitochondrial carrier; adenine nucleotide translocator), member 5 | 292 |
| MG29 or SYPL2 | synaptophysin-like 2 | 284612 |
| NLGN2 | neuroligin 2 | 57555 |
| PRKACA | protein kinase, cAMP-dependent, catalytic, alpha | 5566 |
| FOSB | FBJ murine osteosarcoma viral oncogene homolog B | 2354 |
| SIAT6 | ST3 beta-galactoside alpha-2,3-sialyltransferase 3 | 6487 |
| LOXL2 | lysyl oxidase-like 2 | 4017 |
| PRF1 | perforin 1 (pore forming protein) | 5551 |
| ADPRH | ADP-ribosylarginine hydrolase | 141 |
| APBB3 | amyloid beta (A4) precursor protein-binding, family B, member 3 | 10307 |
| EGR3 | early growth response 3 | 1960 |
| CNR2 | cannabinoid receptor 2 (macrophage) | 1269 |
| IFITM1 | Interferon induced transmembrane protein 1 (9-27) | 8519 |
| PLA2G5 | phospholipase A2, group V | 5322 |
| CAMTA1 | calmodulin binding transcription activator 1 | 23261 |
| SOX4 | SRY (sex determining region Y)-box 4 | 6659 |

TABLE B-continued set of predictive genes.

| Gene Symbol | Gene name | Gene ID |
|---|---|---|
| NFIB | nuclear factor I/B | 4781 |
| NFIC | nuclear factor I/C (CCAAT-binding transcription factor) | 4782 |
| RBMS1 | RNA binding motif, single stranded interacting protein 1 | 5937 |
| G0S2 | G0/G1 switch 2 | 50486 |
| FAT3 | FAT tumor suppressor homolog 3 (Drosophila) | 120114 |
| SLC40A1 | solute carrier family 40 (iron-regulated transporter), member 1 | 30061 |
| GPC6 | glypican 6 | 10082 |
| IGF1R | insulin-like growth factor 1 receptor | 3480 |

Reliability Test of the Candidate Genes and Correlation Between CC Genes Expression Profile and Absence of Pregnancy In order to test the reliability of the 45 gene list, a prospective study was conducted including young (<36 years) normal responder patients referred to our centre for ICSI for male infertility. The embryo selection occurred either according to the gene expression profile in CCs (group 1) or to morphological aspects (group 2 used as control). For each group, two embryos were replaced. For the first 60 patients (30 patients/group), on egg collection day, in group 1, each CC sample was collected individually and processed for gene expression analysis. CC samples (n=267) were analyzed.

Quantitative RT-PCR analysis was performed to measure the relative abundance of the transcripts of interest genes in CCs, and expression data for all biomarkers were obtained from all samples. All patients in both groups had a fresh embryo transfer on day 3. The comparison between the 2 groups reveals significant differences for implantation and ongoing pregnancy rates/pick up (40.0% vs. 26.7% and 70.0% vs. 46.7; p<0.05, respectively). We noted 5 twin pregnancies in group 1 versus 0 in the group 2 used as control. In addition, we observed that there was no relationship between morphological aspects and the CC gene expression profile. On the basis of the analysis of 267 CC samples, we noted 27% of CCs express genes which predict for embryos able to achieve pregnancy, 42% of CCs did not, 31% of CCs showing gene expression for early arrest of embryo development.

Further, data generated from each oocyte (fertilization, embryo development, transfer and pregnancy etc.) were recorded by an embryologist. All patients had two fresh embryos transfer on day 3. Pregnancy was confirmed by the presence of a fetal heartbeat by ultrasound at 6-8 weeks.

CC samples were divided into 3 groups according embryos outcomes. The first group (100% implantation) contained CCs from oocytes that produced a transferred embryo with successful twin pregnancy (n=10). The second group (no pregnancy group) contained CCs from oocytes that resulted in a transferred embryo unable to implant (n=26), group 3 (other: freezing and early embryos arrest) contained CCs from oocytes that produced embryos presenting early arrest before the eight-cell stage or embryos cryopreserved (n=201) and group 4 (50% implantation rate).

The Characteristics of Cumulus Cells Samples

| | 30 patients (age <36 years; ICSI) 267 CCs | | | |
|---|---|---|---|---|
| | | negative groups | | |
| | Positive group Group 1 (100% implantation rate) | Group 2 (0% implantation rate) | Group 3 (other : freezing, early embryos implantation arrest) | Group 4 (50% implantation rate) |
| CCs nbr | 10 | 26 | 201 | 30 |

CCs: Cumulus cells; ICSI: intracytoplasmic sperm injection

Quantitative RT-PCR analysis was performed to measure the relative abundance of the transcripts of genes in CCs and expression data for all 45 genes were obtained from 267 CC samples issued from 30 patients. For each gene, the relative intensity was calculated by dividing the intensity by the average intensity for each patient and for each gene.

Then, a SAM (Significance Analysis of Microarray) was realized to get the more significant genes (p-value <0.05) that distinguish negative groups who didn't have implantation or with early embryo arrest and positive group who got a twin implantation.

Based on these results, 10 genes expression profiles appear to be particularly reliable to predict different clinical conditions: (B) embryo unable to implant and (C) early embryo arrest. These candidate biomarkers are listed in the below Table C.

TABLE C

Clinical conditions predicted by the set of predictive Genes

| Gene Symbol | Gene name | Gene ID |
|---|---|---|
| B: genes whose overexpressions are predictive of embryos unable to implant | | |
| PLA2G5 | phospholipase A2, group V | 5322 |
| GPC6 | glypican 6 | 10082 |
| ATF3 | activating transcription factor 3 | 467 |
| SIAT6 | ST3 beta-galactoside alpha-2,3-sialyltransferase 3 | 6487 |
| PRKACA | protein kinase, cAMP-dependent, catalytic, alpha | 5566 |
| SLC40A1 | solute carrier family 40 (iron-regulated transporter), member 1 | 30061 |
| WNT6 | wingless-type MMTV integration site family, member 6 | 7475 |
| C: genes whose overexpressions are predictive of early embryo arrest | | |
| NFIC | nuclear factor I/C (CCAAT-binding transcription factor) | 4782 |
| RBMS1 | RNA binding motif, single stranded interacting protein | 15937 |
| G0S2 | G0/G1 switch 2 | 50486 |

These biomarkers in cumulus cells were able to predict different clinical conditions. For example, overexpression of PLAG2G5 or GPC6 has been found to be predictive of embryos unable to implant. On contrary, overexpression of NFIC or RBMS1 has been found to be predictive of an early embryo arrest.

In the following step, different box plots (FIG. 1) were achieved for those 10 genes of interest and a superior and an inferior cut-off for each gene were determined, comparing patients with failed implantation or early embryo arrest to patients with twin implantation. When the relative intensity is superior of cut-off, the genes are supposed to discriminate embryos unable to implant or early embryos arrest and those with twin pregnancy.

CONCLUSION

In most mammalian species including human, the cumulus cells which surrounds the oocyte are still present at the time of fertilization in the oviduct and remain until embryonic implantation. Extracellular matrix remodelling within and around the cumulus probably plays a key role in both of these steps. In this respect, we identified 10 genes expressed in cumulus cells that are biomarkers for embryo potential and pregnancy outcome. In our study, we demonstrated that genes expression profile of CC which surrounds oocyte correlated to different outcomes, allowing the identification of a specific expression signature of embryos developing toward pregnancy. In conclusion, we found a differential gene expression between human cumulus cells from oocytes resulting in different pregnancy outcome from patients referred for ICSI or IVF. Our results indicate that analysis of cumulus cells surrounding the oocyte is a non-invasive approach for embryo selection. Typically CC can be collected immediately after oocyte pick-up, the CC can be analyzed with a genomic test (G-test) to assess the potential of the embryo, and the embryo can be then be selected for fresh replacement based on the G-test results.

REFERENCES

Throughout this application, various references describe the state of the art to which this invention pertains. The disclosures of these references are hereby incorporated by reference into the present disclosure.

Assou, S., Anahory, T., Pantesco, V., Le Carrour, T., Pellestor, F., Klein, B., Reyftmann, L., Dechaud, H., De Vos, J., Hamamah, S. (2006) The human cumulus—oocyte complex gene-expression profile. Hum Reprod, 21, 1705-19.

Balaban, B., Urman, B. (2006) Effect of oocyte morphology on embryo development and implantation. Reprod Biomed Online, 12, 608-15.

Brison, D. R., Houghton, F. D., Falconer, D., Roberts, S. A., Hawkhead, J., Humpherson, P. G., Lieberman, B. A., Leese, H J. (2004) Identification of viable embryos in IVF by non-invasive measurement of amino acid turnover. Hum Reprod, 19, 2319-24

Bromer, J. G., Seli, E. (2008) Assessment of embryo viability in assisted reproductive technology: shortcomings of current approaches and the emerging role of metabolomics. Curr Opin Obstet Gynecol, 20, 234-41.

Courtois, G., Smahi, A. (2006) NF-kappaB-related genetic diseases. Cell Death Differ, 13, 843-51.

de Hoon, M. J., Imoto, S., Nolan, J., Miyano, S. (2004) Open source clustering software. Bioinformatics, 20, 1453-4.

Eisen, M. B., Spellman, P. T., Brown, P. O., Botstein, D. (1998) Cluster analysis and display of genome-wide expression patterns. Proc Natl Acad Sci USA, 95, 14863-8.

Fenwick, J., Platteau, P., Murdoch, A. P., Herbert, M. (2002) Time from insemination to first cleavage predicts developmental competence of human preimplantation embryos in vitro. Hum Reprod, 17, 407-12.

Feuerstein, P., Cadoret, V., Dalbies-Tran, R., Guerif, F., Bidault, R., Royere, D. (2007) Gene expression in human cumulus cells: one approach to oocyte competence. Hum Reprod, 22, 3069-77.

Gardner, D. K., Lane, M., Stevens, J., Schoolcraft, W. B. (2001) Noninvasive assessment of human embryo nutrient consumption as a measure of developmental potential. Fertil Steril, 76, 1175-80.

Gasca, S., Pellestor, F., Assou, S., Loup, V., Anahory, T., Dechaud, H., De Vos, J., Hamamah, S. (2007) Identifying new human oocyte marker genes: a microarray approach. Reprod Biomed Online, 14, 175-83.

Hamel, M., Dufort, T., Robert, C., Gravel, C., Leveille, M. C., Leader, A., Sirard, M. A. (2008) Identification of differentially expressed markers in human follicular cells associated with competent oocytes. Hum Reprod, 23, 1118-27.

Haouzi, D., De Vos, J., Loup, V., Assou, S., Gasca, S., Reyftmann, L., Klein, B., Hamamah, S. (2008) [Oocyte and embryo quality: Do the apoptotic markers have a place in the preimplantation genetic diagnostic?]. Gynecol Obstet Fertil, 36, 730-742.

He, B., Chadburn, A., Jou, E., Schattner, E. J., Knowles, D. M., Cerutti, A. (2004) Lymphoma B cells evade apoptosis through the TNF family members BAFF/BLyS and APRIL. J Immunol, 172, 3268-79.

Kolena, J., Kiss, A., Channing, C. P. (1983) Purification of porcine granulosa cells by continuous Percoll gradient. Experientia, 39, 908-9.

Kovalevsky, G., Patrizio, P. (2005) High rates of embryo wastage with use of assisted reproductive technology: a look at the trends between 1995 and 2001 in the United States. Fertil Steril, 84, 325-30.

La Sala, G. B., Nicoli, A., Villani, M. T., Di Girolamo, R., Capodanno, F., Blickstein, I. (2008) The effect of selecting oocytes for insemination and transferring all resultant embryos without selection on outcomes of assisted reproduction. Fertil Steril.

Lee, K. S., Joo, B. S., Na, Y. J., Yoon, M. S., Choi, O. H., Kim, W. W. (2001) Cumulus cells apoptosis as an indicator to predict the quality of oocytes and the outcome of IVF-ET. J Assist Reprod Genet, 18, 490-8.

Lundin, K., Bergh, C., Hardarson, T. (2001) Early embryo cleavage is a strong indicator of embryo quality in human IVF. Hum Reprod, 16, 2652-7.

McKenzie, L. J., Pangas, S. A., Carson, S. A., Kovanci, E., Cisneros, P., Buster, J. E., Amato, P., Matzuk, M. M. (2004) Human cumulus granulosa cell gene expression: a predictor of fertilization and embryo selection in women undergoing IVF. Hum Reprod, 19, 2869-74.

Pearson, H. (2006) Safer embryo tests could boost IVF pregnancy rates. Nature, 444, 12-3.

Perlman, S., Bouquin, T., van den Hazel, B., Jensen, T. H., Schambye, H. T., Knudsen, S., Okkels, J. S. (2006) Transcriptome analysis of FSH and FSH variant stimulation in granulosa cells from IVM patients reveals novel regulated genes. Mol Hum Reprod, 12, 135-44.

Reddy, U. M., Wapner, R. J., Rebar, R. W., Tasca, R. J. (2007) Infertility, assisted reproductive technology, and adverse pregnancy outcomes: executive summary of a National Institute of Child Health and Human Development workshop. Obstet Gynecol, 109, 967-77.

Reme, T., Hose, D., De Vos, J., Vassal, A., Poulain, P. O., Pantesco, V., Goldschmidt, H., Klein, B. (2008) A new method for class prediction based on signed-rank algorithms applied to Affymetrix microarray experiments. BMC Bioinformatics, 9, 16.

Sakkas, D., Gardner, D. K. (2005) Noninvasive methods to assess embryo quality. Curr Opin Obstet Gynecol, 17, 283-8.

Sasson, R., Dantes, A., Tajima, K., Amsterdam, A. (2003) Novel genes modulated by FSH in normal and immortalized FSH-responsive cells: new insights into the mechanism of FSH action. Faseb J, 17, 1256-66.

Sasson, R., Rimon, E., Dantes, A., Cohen, T., Shinder, V., Land-Bracha, A., Amsterdam, A. (2004) Gonadotrophin-induced gene regulation in human granulosa cells obtained from IVF patients. Modulation of steroidogenic genes, cytoskeletal genes and genes coding for apoptotic signalling and protein kinases. Mol Hum Reprod, 10, 299-311.

Scott, L., Alvero, R., Leondires, M., Miller, B. (2000) The morphology of human pronuclear embryos is positively related to blastocyst development and implantation. Hum Reprod, 15, 2394-403.

Seli, E., Sakkas, D., Scott, R., Kwok, S. C., Rosendahl, S. M., Burns, D. H. (2007) Noninvasive metabolic profiling of embryo culture media using Raman and near-infrared spectroscopy correlates with reproductive potential of embryos in women undergoing in vitro fertilization. Fertil Steril, 88, 1350-7.

Steele-Perkins, G., Plachez, C., Butz, K. G., Yang, G., Bachurski, C. J., Kinsman, S. L., Litwack, E. D., Richards, L. J., Gronostajski, R. M. (2005) The transcription factor gene Nfib is essential for both lung maturation and brain development. Mol Cell Biol, 25, 685-98.

Stein, J. V., Lopez-Fraga, M., Elustondo, F. A., Carvalho-Pinto, C. E., Rodriguez, D., Gomez-Caro, R., De Jong, J., Martinez, A. C., Medema, J. P., Hahne, M. (2002) APRIL, modulates B and T cell immunity. J Clin Invest, 109, 1587-98.

Su, Y. Q., Sugiura, K., Wigglesworth, K., O'Brien, M. J., Affourtit, J. P., Pangas, S. A., Matzuk, M. M., Eppig, J. J. (2008) Oocyte regulation of metabolic cooperativity between mouse cumulus cells and oocytes: BMP15 and GDF9 control cholesterol biosynthesis in cumulus cells. Development, 135, 111-21.

Sugiura, K., Su, Y. Q., Diaz, F. J., Pangas, S. A., Sharma, S., Wigglesworth, K., O'Brien, M. J., Matzuk, M. M., Shimasaki, S., Eppig, J. J. (2007) Oocyte-derived BMP15 and FGFs cooperate to promote glycolysis in cumulus cells. Development, 134, 2593-603.

Tusher, V. G., Tibshirani, R., Chu, G. (2001) Significance analysis of microarrays applied to the ionizing radiation response. Proc Natl Acad Sci USA, 98, 5116-21.

Van Montfoort, A. P., Dumoulin, J. C., Kester, A. D., Evers, J. L. (2004) Early cleavage is a valuable addition to existing embryo selection parameters: a study using single embryo transfers. Hum Reprod, 19, 2103-8.

van Montfoort, A. P., Geraedts, J. P., Dumoulin, J. C., Stassen, A. P., Evers, J. L., Ayoubi, T. A. (2008) Differential gene expression in cumulus cells as a prognostic indicator of embryo viability: a microarray analysis. Mol Hum Reprod, 14, 157-68.

Yang, W. J., Hwu, Y. M., Lee, R. K., Li, S. H., Lin, S. Y., Fleming, S. (2007) Early cleavage does not predict treatment outcome following the use of GnRH antagonists in women older than 35. Fertil Steril, 88, 1573-8.

Zhang, X., Jafari, N., Barnes, R. B., Confino, E., Milad, M., Kazer, R. R. (2005) Studies of gene expression in human cumulus cells indicate pentraxin 3 as a possible marker for oocyte quality. Fertil Steril, 83 Suppl 1, 1169-79.

Zhu, X. M., Zhu, Y. M., Xu, C. M., Qian, Y. L., Jin, F., Huang, H. F. (2007) Autologous mature follicular fluid: its role in in vitro maturation of human cumulus-removed oocytes. Fertil Steril.

Assou S., Haouzi D., Mahmoud K., Aouacheria A., Guillemin Y., Pantesco V., Reme T., Dechaud H., De vos J., Hamamah S. (2008) A non invasive test for assessing embryo potential by gene expression profiles of human cumulus cells: a proof of concept study. Molecular human reproduction, Vol. 14, n° 12 pp. 711-719, December 2008.

Fourar M., Haouzi D., Aouacheria A., Dechaud h., Bendhaou k., Hamamah S. (2008) Gene expression profiles of human cumulus cells and pregnancy outcome identification of molecular biomarkers of embryo competence, Fertility and Sterility, vol. 90, 1 September 2008, p. S72, Abstract.

The invention claimed is:

1. A method of implanting an embryo in a female undergoing in vitro fertilization, comprising the steps of:
    a) collecting at least one oocyte with its cumulus cells from said female;
    b) measuring, in said cumulus cells surrounding said oocyte, an expression level of each of the 10 genes ATF3, SIAT6, PRKACA, PLA2G5, GPC6, G0S2, RBMS1, NFIC, SLC40A1 and WNT6;
    c) comparing the expression level of each of the 10 genes in the cumulus cells with control expression levels of the 10 genes from cumulus cells associated with competent oocytes;
    d) assessing said oocyte as having a higher probability of being competent if a cumulus cell surrounding the oocyte does not overexpress any of the 10 genes when compared to cumulus cells associated with a competent oocytes;
    e) fertilizing said oocyte having a higher probability of being competent in vitro to generate an embryo; and
    f) implanting said embryo in said female.

2. The method of claim 1, wherein said step of measuring is carried out by
    i) extracting total mRNA from said cumulus cells; and
    ii) amplifying said mRNA to form cDNA using primers that are specific for said mRNA.

3. The method of claim 1, wherein said step of measuring is carried out with nucleic acid probes.

4. A method of implanting an embryo in a female undergoing in vitro fertilization, comprising the steps of:
    a) collecting oocytes from said female;
    b) generating embryos from said oocytes by fertilizing said oocytes in vitro;
    c) measuring, in cumulus cells surrounding each of said embryos, an expression level of each of the 10 genes ATF3, SIAT6, PRKACA, PLA2G5, GPC6, G0S2, RBMS1, NFIC, SLC40A1 and WNT6;
    d) comparing the expression level of each of the 10 genes in the cumulus cells with control expression levels of the 10 genes from cumulus cells associated with competent oocytes;
    e) assessing an embryo as having a higher probability of being competent if a cumulus cell associated with the embryo does not overexpress any of the 10 genes when compared to cumulus cells associated with competent oocytes; and
    f) implanting said embryo having a higher probability of being competent in said female.

5. The method of claim 4, wherein said step of measuring is carried out by
    i) extracting total mRNA from said cumulus cells; and
    ii) amplifying said mRNA to form cDNA using primers that are specific for said mRNA.

6. The method of claim 4, wherein said step of measuring is carried out with nucleic acid probes.

* * * * *